United States Patent [19]

Taylor et al.

[11] 4,260,746

[45] Apr. 7, 1981

[54] CHEMICAL INTERMEDIATES USEFUL TO PREPARE CEPHALOSPORINS

[75] Inventors: Andrew W. Taylor, Dorking; George Burton, Sutton; John P. Clayton, Horsham, all of England

[73] Assignee: Beecham Group Limited, England

[21] Appl. No.: 85,039

[22] Filed: Oct. 15, 1979

Related U.S. Application Data

[62] Division of Ser. No. 810,330, Jun. 27, 1977, Pat. No. 4,202,973.

[30] Foreign Application Priority Data

Jun. 26, 1976 [GB] United Kingdom ............... 26684/76

[51] Int. Cl.$^3$ ................. C07D 501/20; C07D 501/36; C07D 501/04
[52] U.S. Cl. ..................................... 544/021; 544/22; 544/24; 544/25; 544/27; 544/28; 544/30; 424/246
[58] Field of Search ...................... 544/28, 21, 27, 22, 544/29, 30,

[56] References Cited

U.S. PATENT DOCUMENTS

| 3,843,641 | 10/1974 | Christensen et al. | 544/21 |
|---|---|---|---|
| 3,860,585 | 1/1975 | Carroll et al. | 260/306.7 C |
| 3,960,845 | 9/1977 | Yanagisawa et al. | 544/21 |
| 4,014,873 | 3/1977 | Christensen et al. | 544/21 |
| 4,051,299 | 9/1977 | Shimizu et al. | 544/21 |
| 4,051,320 | 9/1977 | Yanagisawa et al. | 544/21 |
| 4,058,661 | 11/1977 | Cama et al. | 544/21 |
| 4,086,423 | 4/1978 | Firestone et al. | 544/21 |

FOREIGN PATENT DOCUMENTS 2534946 3/1976 Fed. Rep. of Germany .

*Primary Examiner*—Nicholas S. Rizzo
*Attorney, Agent, or Firm*—Jacobs & Jacobs

[57] ABSTRACT

7α-Methoxy-7β-acylamino cephalosporins are prepared from 7β-acylamino cephalosporins through formation of a ketenimine by the action of an acid halide, formation of an addition reaction adduct of this ketenimine, treatment of the adduct with a methoxide to form a 7α-methoxy ketenimine and hydrolysis of the latter ketenimine.

15 Claims, No Drawings

CHEMICAL INTERMEDIATES USEFUL TO PREPARE CEPHALOSPORINS

CROSS-REFERENCE

This is a division of Ser. No. 810,330 filed June 27, 1977, now U.S. Pat. No. 4,202,973.

DETAILED DESCRIPTION

This invention relates to a class of intermediates useful for the preparation of antibacterially active cephalosporin derivatives, in particular 7α-methoxy cephalosporin having a carboxylic acid function at the 2-position in the side chain. The invention also relates to a process for the preparation of the novel intermediates and to a process for their conversion to the cephalosporin.

British Pat. No. 1,463,468 discloses a process for the preparation of 7-alkoxy cephalosporins which comprises reacting a cephalosporin having a hydroxy or halo group on the 2-position of the side chain with a halogenating agent to form a 2,3-dihaloimine and subsequently reacting this with an alkali metal alkoxide to give a 7-alkoxyketenimine which is hydrated to give the required product. One disadvantage of this process is that the hydroxy- or halo-cephalosporin starting material must be prepared by acylation of 7-amino cephalosporanic acid with the corresponding side chain. The process does not provide a method for the introduction of a 7α-alkoxy substituent directly into a 7-acylaminocephalosporin.

Furthermore, in the above process the 2,3-dihaloimine intermediate must be isolated in order to remove excess halogenating agent (such as phosphorus pentachloride) therefrom prior to treatment with the alkali metal alkoxide. However, in the case of cephalosporin derivatives having a carboxylic acid function at the 2-position, the dihaloimine is thermally unstable and the process is therefore unsuitable for that class of cephalosporins.

West German Offenlegungsschrift No. 2,534,946 discloses a related process for the preparation of 7-alkoxy cephalosporins via a ketenimine intermediate. The ketenimine is prepared by reacting a 7-acylamino cephalosporin with a halogenating agent and treating the resulting imino halide with a base to give a ketenimine. Although the scope of the disclosure covers the case of cephalosporins having alkoxycarbonyl groups at the 2-position of the side chain, there is no specific example described therein of a cephalosporin bearing a 2-carboxylic acid or ester group on the side chain.

We have now found that for a small group of cephalosporins derivatives bearing a carboxylic acid or ester substituent at the 2-position on the side chain, a ketenimine intermediate can be produced directly from the 7-acylaminocephalosporin without the intermediate isolation of an imino-halide and without the need for a separate treatment with a base. This group of ketenimine intermediate therefore, have advantages over the broad class of intermediates disclosed in Offenlegungsschrift No. 2,534,946.

Accordingly, the present invention provides a ketenimine of formula (I):

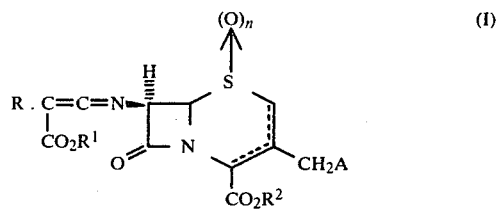

wherein R represents a furyl, thienyl, cycloalkyl, cycloalkenyl, or phenyl group, or a phenyl group substituted by from 1 to 3 hydroxy, halogen, nitro, $C_{1-6}$alkyl, $C_1-C_6$alkoxy, amino or carboxy groups;

$R^1$ represents an ester-forming radical;

$R^2$ represents an in vivo hydrolysable ester radical or a carboxyl-blocking group;

A represents hydrogen, pyridyl, acetoxy, carbamoyloxy or a heterocyclicthio group;

n is zero or 1 and the dotted line represents a double bond at either the 2- or 3-positions.

The group A may advantageously be a group of formula:

—S— Het;

wherein "Het" is a five or six-membered heterocyclic ring containing from 1 to 4 atoms selected from N, O, and S unsubstituted or substituted with one or two groups selected from $C_{1-6}$alkyl, $C_1-C_6$alkenyl, $C_1-C_6$alkoxy, hydroxyalkyl, alkoxyalkyl, carboxyalkyl, carbamoyl, carbamoylmethyl, trifluoromethyl, hydroxy, and halogen.

Examples of the group "Het" include unsubstituted and substituted diazolyl, triazolyl, tetrazolyl, thiazolyl, thiadiazolyl, thiatriazolyl, oxazolyl, and oxadiazolyl groups. Suitable groups "Het" include unsubstituted and substituted 1,2,3-triazolyl; 1,2,4-triazolyl; 1,2,3,4-tetrazolyl; oxazolyl; thiazolyl; 1,3,4-oxadiazolyl; 1,3,4-thiadiazolyl, or 1,2,4-thiadiazolyl.

Preferably, A is 2-methyl-1,3,4-thiadiazol-5-ylthio; 1-methyl-(1H)-1,2,3,4-tetrazol-5-ylthio; 2-methyl-1,3,4-oxadiazol-5-ylthio; or (1H)-1,3,4-triazol-5-ylthio.

Preferably, n is zero and the dotted line in formula (I) represents a double bond in the 3-position.

Suitable groups R include 2- and 3-furyl, 2- and 3-thienyl, cyclopropyl, cyclobutyl, cyclopentyl, cyclohexyl, cyclobutenyl, cyclopentenyl, cyclohexenyl, cyclohexa-1,4-dienyl, phenyl, 4-hydroxyphenyl, 3-chloro-4-hydroxyphenyl, 3,4-dihydroxyphenyl.

Most suitably R is 2- or 3-thienyl, phenyl or 4-hydroxyphenyl; preferably, phenyl.

In vivo hydrolysable pharmaceutically acceptable ester forming radicals for the group $R^2$ are those which, when attached at that position on a cephalosporin nucleus, hydrolyse readily in the human body to produce the parent acid. It is well established that simple alkyl and aryl esters of cephalosporins fail to meet this requirement as they are resistant to hydrolysis by human tissues. Examples of suitable in vivo hydrolysable ester radicals for the group $R^2$ include acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; and lactone, thiolactone and dithiolactone groups, i.e. ester groups of formula:

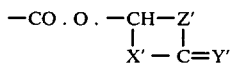

$$-CO.O.-CH-Z'$$
$$\qquad\quad |\quad\;\; |$$
$$\qquad\quad X'-C=Y'$$

wherein X' and Y' are oxygen of sulphur and Z' is an ethylene group or a 1,2-phenylene group optionally substituted by lower-alkoxy, halogen or nitro.

Preferred ester groups are the phthalide and 5,6-dimethoxyphthalide esters.

Suitable carboxyl-blocking derivatives for the group $R^2$ in formula (I), include salts, ester, and anhydride derivatives of the carboxylic acid. The derivative should be one which may readily be cleaved at a later stage of the reaction. Suitable salts include tertiary amine salts, such as those with tri-loweralkylamines, N-ethyl-piperidine, 2,6-lutidine, pyridine, N-methylpyrrolidine, dimethylpiparazine. A preferred salt is with triethylamine.

Suitable carboxyl-blocked groups of formula $CO_2R^2$ include the following:

(i) —$COOCR_cR_dR_e$ wherein at least one of $R_c$, $R_d$ and $R_e$ is an electron-donor e.g. p-methoxyphenyl, 2,4,6-trimethylphenyl, 9-anthryl, methoxy, acetoxy, methoxymethyl, benzyl or fur-2-yl. The remaining $R_c$, $R_d$ and $R_e$ groups may be hydrogen or organic substituting groups. Suitable ester groups of this type include p-methoxybenzyloxy-carbonyl, 2,4,6-trimethylbenzyloxy carbonyl, bis(p-methoxyphenyl)methoxycarbonyl, 3,5-di-t-butyl-4-hydroxybenzyloxycarbonyl, methoxymethoxycarbonyl and benzyloxycarbonyl.

(ii) —$COOCR_cR_dR_e$ wherein at least one of $R_c$, $R_d$ and $R_e$ is an election-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R_c$, $R_d$ and $R_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —$COOCR_cR_dR_e$ wherein at least two of $R_c$, $R_d$ and $R_e$ are hydrocarbons such as alkyl e.g. methyl or ethyl, aryl, e.g. phenyl and the remaining $R_c$, $R_d$ and $R_e$ group, if there is one, is hydrogen. Suitable esters of this type include t-butyloxycarbonyl, t-amyloxycarbonyl, diphenylmethoxycarbonyl and triphenylmethoxycarbonyl.

(iv) —$COOCR_f$ wherein $R_f$ is adamantyl, 2-benzyloxyphenyl, 4-methylthiophenyl, tetrahydrofur-2-yl-tetrahydropyran-2-yl, pentachlorophenyl;

(v) Silyloxycarbonyl groups obtained by reaction of a silylating agent as described above with the carboxylic acid group;

(vi) $COOP.R_aR_b$, wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

The carboxyl group may be regenerated from any of the above esters by usual methods for example, acid- —and base—catalysed hydrolysis, or by enzymically—catalysed hydrolysis. Alternative methods of cleavage include:

reaction with Lewis acids, such as trifluoroacetic acid, formic acid, hydrochloric acid in acetic acid, zinc bromide in benzene and aqueous solutions or suspensions of mercuric compounds. (The reaction with the Lewis acid may be facilitated by addition of a nucleophile such as anisole);

reduction with agents such as zinc/acetic acid, zinc/formic acid, zinc/lower alcohol, zinc/pyridine, palladised-charcoal and hydrogen, and sodium and liquid ammonia;

attack by nucleophiles, such as those containing a nucleophilic oxygen or sulphur atom for example alcohols, mercaptans and water; oxidative methods, for example, those which involve the use of hydrogen peroxide and acetic acid; and irradiation.

The group $R^1$ may be any ester-forming radical as hydrolysis to the free acid at that position is not essential for the activity of the eventually produced cephalosporin derivative. The group $R^1$ may therefore be any of the radicals described above as being in vivo hydrolysable when present at the 4-position of the cephalosporin-nucleus; or it be any of the above-mentioned carboxyl-blocking groups.

In addition the group $R^1$ may be an alkyl, cycloalkyl, alkenyl, alkynyl, aryl, or heterocyclic group any of which may be substituted. Suitable such groups include:

(a) alkyl especially $C_{1-6}$ alkyl such as methyl, ethyl, n- and iso-propyl, n-, sec-, iso- and tert-butyl, and pentyl;

(b) substituted $C_{1-6}$ alkyl wherein the substituent is at least one of: chloro, bromo, fluoro, nitro, carbo ($C_{1-6}$ alkoxy), $C_{1-6}$ alkanoyl, $C_{1-6}$ alkoxy, cyano, $C_{1-6}$ alkylmercapto, ($C_{1-6}$ alkylsulfinyl, $C_{1-6}$ alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl)piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, of substituted N-alkylanilino wherein the substituent is chloro, bromo, $C_{1-6}$ alkyl or $C_{1-6}$ alkoxy;

(c) cycloalkyl and ($C_{1-6}$ alkyl) substituted cycloalkyl having from 3 to 7 carbon atoms in the cycloalkyl moiety;

(d) alkenyl having up to 8 carbon atoms;

(e) alkynyl having up to 8 carbon atoms;

(f) phenyl and substituted phenyl wherein the substituent is at least one of chloro, bromo, fluoro, $C_{1-6}$ alkoxy, $C_{1-6}$ alkanoyl, carbo-($C_{1-6}$)alkoxy, nitro, or di($C_{1-6}$)alkyl amino;

(g) benzyl or substituted benzyl wherein the substituent is chloro, bromo, fluoro, $C_{1-6}$ alkyl, $C_{1-6}$ alkoxy, $C_{1-6}$ alkanoyl carbo($C_{1-6}$)alkoxy, nitro, or di($C_{1-6}$)alkyamino;

(h) heterocyclic groups such as: furyl, quinolyl, methyl-substituted quinolyl, phenazinyl, 1,3-benzodioxolyl, 3-(2-methyl-γ-pyronyl), 3-(γ-pyronyl) or methylpyridyl;

(i) other hydrocarbyl groups such as: ac-indanyl and substituted derivatives thereof wherein the substituent is methyl, chloro or bromo; ac-tetrahydronaphthyl and substituted derivatives thereof wherein the substituent is methyl, chloro or bromo; benzohydryl, trityl, cholesteryl, or bicyclo[4.4.0]decyl.

Preferred groups for $R^1$ include $C_{1-6}$ alkyl, benzyl, phthalidyl, indanyl, phenyl, mono-, di-, and tri-($C_1$–$C_6$)-alkyl substituted phenyl such as o-, m or p-methylphenyl, ethylphenyl, n- or iso-propylphenyl, n-, sec-, iso- or t-butylphenyl.

The intermediate of formula (I) may be prepared by reacting a 7-acylaminocephalosporin of formula (II):

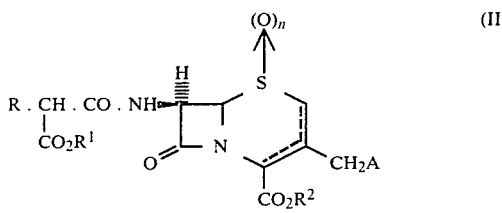

wherein R, $R^1$, $R^2$, n and A are as defined with respect to formula (I) above; with an acid halide.

Suitably, the reaction with acid halide is carried out in the presence of an acid binding agent such as tertary amine, e.g. pyridine, triethylamine or N,N-dimethylaniline.

Examples of suitable acid halides are phosphorus pentachloride, phosgene, phosphorus pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from +5° to −30° C. (preferably about 0° C.) when phosphorus pentachloride is employed. The amount of the tertiary amine is preferably 3–5 mols per mole of phosphorus pentachloride. It is also preferable to use the phosphorus halide in an amount in excess of that of the starting material.

The value of the ketenimine compounds of formula (I) derives from their use in the preparation of 7-methoxy cephalosporins.

Thus, in a further aspect, the present invention provides a process for preparing a compound of formula (III):

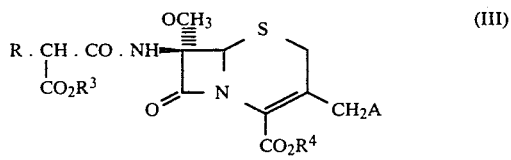

wherein R and A are as defined above with respect to formula (I);

$R^3$ represents hydrogen, a pharmaceutically acceptable salt-forming ion or ester-forming radical; and $R^4$ represents hydrogen, a pharmaceutically acceptable salt-forming ion or an in vivo hydrolysable ester-forming radical; which process comprises:

(a) reacting a ketenimine of formula (I) with a double bond addition reagent;
(b) reacting the resulting product with a compound of formula $CH_3OM$, wherein M is an alkali metal or thallium;
(c) hydrolysing the resulting product;
(d) removing any carboxyl-blocking groups;
(e) optionally salifying or esterifying any free carboxylic acid group;
(f) converting a $\Delta^2$ isomer into the desired $\Delta^3$ isomer; and
(g) reducing a sulphoxide compound (n=1) to form the desired sulphide compound (n=0).

Suitable salt-forming ions for the groups $R^3$ and $R^4$ include metal ions e.g. aluminium, alkali metal ions such as sodium or potassium, alkaline earth metal ions such as calcium or magnesium, and ammonium or substituted ammonium ions for example those from lower alkylamines such as 2-hydroxyethylamine, bis-(2-hydroxyethyl)-amine or tri-(2-hydroxyethyl)-amine, cycloalkylamines such as bicyclohexylamine, or from procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with benzylpenicillin.

The double bond addition reagent is a difunctional moiety where each of the groups can be displaced by nucleophiles.

Suitable double bond addition reagents for the above process include diatomic halogen molecules or a compound of formula $Br.N_3$. If this double bond addition reagent is designated X–Y, the adduct formed has the formula (IV):

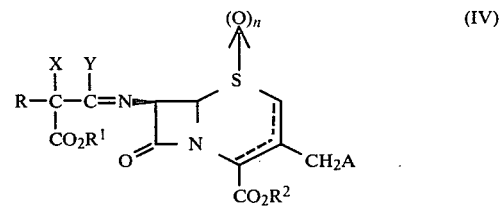

Suitably, both X and Y are halogen, preferably bromine, as the reaction proceeds more smoothly.

The reaction is suitably carried out in an inert solvent, such as tetrahydrofuran or a halogenated hydrocarbon e.g. chloroform at low temperatures preferably −20° C. to −70° C., e.g. at about −50° C.

The compound of formula (IV) is then reacted with an alkali metal methoxide of formula $CH_3O.M$. Suitably the alkali metal M may be sodium or potassium, but is preferably lithium. The reaction is generally carried out in an alcoholic solvent, preferably methanol, optionally in the presence of another inert solvent, such as tetrahydrofuran. The reaction is suitably carried out at low temperature, preferably in the range of −40° to −85°, preferably about −75°. The reagent $CH_3O.M.$ may be formed in situ by the use of methanol together with a base such as butyl lithium, lithium diisopropylamide, lithium or sodium hydride or preferably butyl lithium.

The thus produced 7-α-methoxy ketenimine of formula (V):

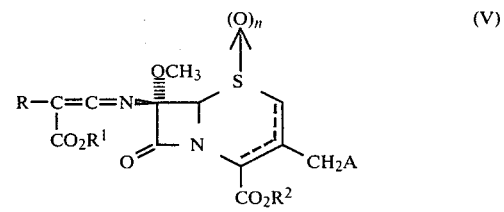

is then hydrolysed.

Preferably, this hydrolysis is carried out at a pH in the range of 1–5, preferably pH 2–4, at ambient temperature.

The ketenimine compounds of formula (I) are also useful intermediates for the preparation of other 7-substituted cephalosporins.

Thus a compound of formula (VI):

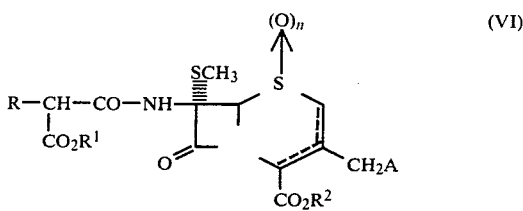

[wherein R, $R^1$, $R^2$ and A are as defined with respect to formula (I)] may be prepared by:

(a) reacting a ketenimine of formula (I) with a compound of formula MeS—Z, wherein Z is a readily displaceable group; to produce a compound of formula (VII):

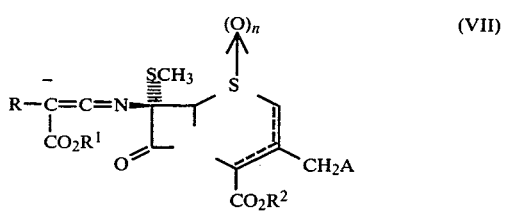

and;

(b) hydrolysing the compound of formula (VII) to produce a 7-methylthio cephalosporin, of formula (VI).

A suitable readily displaceable group Z is the group —$SO_2CH_3$, and the reaction of compound (I) with compound MeS-Z is generally carried out at low temperature, suitably in the range +5° to −30° C., preferably, about 0° C.

The thiomethyl cephalosporins of formula (VI) are themselves useful intermediates for the preparation of other 7-substituted cephalosporins, including the methoxy-substituted compounds (III), by methods known in the art, for example by treatment with mercuric chloride and methanol.

The following examples illustrate the preparation of ketenimine intermediates of this invention and its use in preparing antibacterially active cephalosporins.

EXAMPLE 1

Preparation of benzhydryl 7β-(2'-p-methylphenoxycarbonyl-2'-thien-3-yl)ketenimino-3-acetoxymethylceph-3-em-4-carboxylate Benzhydryl 7β-(2'-p-methylphenoxycarbonyl-2'-thien-3-yl)-acetamido-3-acetoxymethylceph-3-em-4-carboxylate (2.2 g., 3.0 mmol) in chloroform (10 ml) was treated with pyridine (2.61 ml) added at 0° C. Phosphorus pentachloride (2.04 g., 10 mmol) in chloroform (40 ml) was added slowly with stirring at 0° C. After three hours at 0° C., the solution was filtered. The solids were washed with ethyl acetate, and the combined organic layers washed successively with water and sodium bicarbonate solution, dried ($Na_2SO_4$) and evaporated to give almost pure title compound (1.79 g) $\nu$max ($CHCl_3$) 2020, 1790, 1720 cm$^{-1}$. δ ($CDCl_3$) 1.98 (3H,s,—$OCOCH_3$), 2.32 (3H,s,Ar$CH_3$), 3.40 (2H,m, $C_2$ methylene), 4.91 (3H, complex, —$CH_2OCO$— and $C_6$-proton), 5.77 (1H,d,J 4 Hz, $C_7$-proton), 6.9–7.6 (18H, complex, benzhydryl, aryl and thienyl protons).

EXAMPLE 2

Preparation of benzhydryl 7α-methoxy-7β-(2'-p-methylphenoxycarbonyl-2'-thien-3-yl)ketenimino-3-acetoxymethylceph-3-em-carboxylate The ketenimine from example 1 (0.29 g, 0.42 mmole) in tetrahydrofuran (T.H.F.) (10 ml) at −75° C. was treated with bromine (0.23 ml, 0.42 mmole), and the solution stirred for 30 minutes. Lithium methoxide (0.042 g, 1.10 mmol) in methanol (0.77 ml) was added at −75°. After 20 minutes acetic acid (0.5 ml) was added and cooling discontinued. Ethyl acetate was added and the organic layer washed with sodium bicarbonate and brine, dried and evaporated to give the crude title compound (0.21 g). Purification by chromatography on silica (petrol/ethyl acetate) gave 38% overall yield, $\nu$max ($CHCl_3$) 2010, 1790, 1730, 1500 cm$^{-1}$. δ ($CDCl_3$) 1.87 (3H,s, —$OCOCH_3$), 2.20 (3H,s, Ar$CH_3$), 2.15 (2H,m, $C_2$ methylene), 2.57 (3H,s, —$OCH_3$), 4.6–5.0 (3H,m, —$CH_2OCO$— and $C_6$-proton), 6.8–7.7 (18H, complex, benzhydryl, aromatic and thienyl protons).

EXAMPLE 3

Preparation of 2'-epimers of benzhydryl 7α-methoxy-7β-(2'-p-methylphenoxycarbonyl-2'-thien-3-yl)acetamido-3-acetoxymethylceph-3-em-4-carboxylate The ketenimine from Example 2 (0.14 g, 0.19 mmol) was dissolved in T.H.F. (10 ml) containing water (1 ml) and sufficient $H_3PO_4$ to lower the pH to 2.5. After standing for three days at room temperature, ethyl acetate was added. The organic layer was washed with water, dried and evaporated to give the title compound (0.13 g). Purification by chromatography on silica (petrol/ethyl acetate) gave 80% yield, $\nu$max ($CHCl_3$) 3350, 1780, 1725, 1690 cm$^{-1}$. δ ($CDCl_3$) 1.93 (3H,s,—$OCOCH_3$), 2.25 (3H,s, Ar$CH_3$), 3.20 (2H,m, $C_2$ methylene), 3.35, 3.38 (3H,2s, —$OCH_3$), 4.6–5.0 (4H, complex, —$CH_2OCO$—, —$CHCONH$— and $C_6$-protons), 6.9–7.7 (19H, complex benzhydryl, aromatic,thienyl, and —NH— protons).

EXAMPLE 4

Preparation of p-bromophenacyl 7β-(2'-p-methylphenoxycarbonyl-2'-thien-3-yl)ketenimino-3-acetoxymethylceph-3-em-4-carboxylate p-bromophenacyl 7β-(2'-p-methylphenoxycarbonyl-2'-thien-3-yl)-acetamido-3-acetoxymethylceph-3-em-4-carboxylate. (5.0 g, 6.7 mmol) in chloroform (100 ml) at 0° C., was treated with pyridine (5.83 ml). Phosphorus pentachloride (4.56 g, 22 mmol) in chloroform (60 ml) was added slowly (one hour) with vigorous stirring, at 0° C. After a further three hours at 0° C., the solution was concentrated, diluted with ethyl acetate and washed successively with water and sodium bicarbonate solution. The organic layer was dried and evaporated to give almost pure title compound (4.33 g, 89%), $\nu$max ($CHCl_3$) 2030, 1790, 1735, 1710 cm$^{-1}$. δ ($CDCl_3$) 2.09 (3H,s,—$OCOCH_3$), 2.33 (3H,s,Ar$CH_3$), 3.59 (2H,s,$C_2$methylene), 5.20 (3H, complex, —$CH_2OCO$— and $C_6$-proton), 5.57 (2H,s, —$CO_2CH_2$—), 5.84 (1H,d,J 5 Hz, $C_7$-proton), 7.0–8.1 (11H, m, aromatic and thienyl protons).

EXAMPLE 5

Preparation of p-bromophenacyl
7α-methoxy-7β-(2'-p-methylphenoxycarbonyl-2'-thien-3-yl)ketenimino-3-acetoxymethyl-ceph-3-em-4-carboxylate The ketenimine from Example 4 (4.33 g., 5.96 mmol) in THF (120 ml) at −50° C., was treated with bromine (0.326 ml, 5.95 mmol). After 10 minutes the solution was cooled to −70° C. Lithium methoxide (0.84 g, 22 mmol) in methanol (15 ml) was added dropwise at −70° C. and stirred a further 20 minutes. Acetic acid (3 ml) was added and cooling discontinued. Ethyl acetate was added and the organic layer washed with sodium bicarbonate and brine, dried and evaporated to give the title compound (3.84 g) $\nu$max (CHCl$_3$) 2030, 1790, 1730, 1710 cm$^{-1}$. $\delta$ (CDCl$_3$) 2.07 (3H,s,—OCOCH$_3$), 2.33 (3H,s,ArCH$_3$), 3.45 (2H,m, C$_2$methylene), 3.75 (3H,s, —OCH$_3$), 5.15 (3H, complex, —CH$_2$OCO— and C$_6$-proton), 5.55 (2H,s, —CO$_2$CH$_2$—), 6.9–8.0 (11H,m, aromatic and thienyl protons).

EXAMPLE 6

Preparation of 2'-epimers of p-bromophenacyl
7α-methoxy-7β-(2'-p-methylphenoxycarbonyl-2'-thien-3-yl)acetamido-3-acetoxyceph-3-em-4-carboxylate The ketenimine from Example 5 (3.84 g, 5.07 mmol) was dissolved in THF (20 ml) containing water (2 ml) and sufficient H$_3$PO$_4$ to lower the pH to 2.5. After standing for three days at room temperature, ethyl acetate was added. The organic layer was washed with water, dried and evaporated to give a quantative recovery of the title compound, $\nu$max (CHCl$_3$) 3330, 3270, 1780, 1740, 1710 cm$^{-1}$. $\delta$ (CDCl$_3$) 2.09 (3H,s, —OCOCH$_3$), 2.32 (3H,s,ArCH$_3$), 3.46, 3.50 (3H,2s,—OCH$_3$), 3.60 (2H,m, C$_2$methylene), 5.12 (4H, complex, —CH$_2$OCO—, —CHCONH— and C$_6$-proton), 5.50 (2H,s, —CO$_2$CH$_2$—), 7.0–8.0 (12H, complex, aromatic, thienyl, and —NH— protons).

EXAMPLE 7

Preparation of 2'-epimers of
7α-methoxy-7β-(2'-p-methylphenoxycarbonyl-2'-thien-3-yl)acetamido-3-acetoxymethylceph-3-em-4-carboxylic acid The p-bromophenacyl ester from Example 6 (3.21 g., 4.14 mmol) in dimethylformamide (85 ml): acetic acid (21 ml) was stirred with zinc dust (7 g) for one hour at room temperature. The solution was filtered, and solids washed with ethyl acetate. The organic layer was washed with water and evaporated. The residue was dissolved in sodium bicarbonate solution and washed with ethyl acetate. The aqueous layer was acidified to pH 1.5 and extracted with ethyl acetate. The organic layer was washed with brine, dried and evaporated to give the title compound (1.10 g, 47%), $\nu$max (CHCl$_3$) 3260, 1780, 1760, 1710 cm$^{-1}$. $\delta$ (CDCl$_3$) 2.05 (3H,s,—OCOCH$_3$), 2.33 (3H,s, ArCH$_3$), 3.2–3.7 (5H, complex, C$_2$methylene and —OCH$_3$), 4.9–5.4 (4H, complex, —CH$_2$OCO—, CHCONH and C$_6$-proton), 6.9–8.0 (12H, complex,aromatic, thienyl, and —NH— protons).

EXAMPLE 8

Preparation of 2'-epimers pf
7α-methoxy-7β-(2'carboxy-2'-thien-3-yl)acetamido-3-(1-methyl-1H-tetrazol-5-ylthio)methylceph-3-em-4-carboxylic acid The acetoxy cephalosporin from Example 7 (0.31 g., 0.55 mmol) in water (25 ml): acetone (10 ml) at 70° C. was treated with 5-mercapto-1-methyl-1H-tetrazole (0.06 g., 0.5 mmol). The pH of the solution was raised to 5.0 by addition of sodium hydroxide solution and maintained at pH 5.0 throughout the reaction by further additions. The solution was stirred at 70° C. for fourteen hours, cooled and acidified to pH 1.5. The aqueous layer was extracted with ethyl acetate. The organic layer was washed with brine, dried and evaporated to give the crude title compound (0.18 g). $\delta$ (CDCl$_3$) 3.45 3.53 (3H,2s,—OCH$_3$), 3.6–3.8 (2H,m, C$_2$methylene), 4.00 (3H,s, N—CH$_3$), 4.4–4.6 (2H,m, —CH$_2$S—), 5.1–5.3 (2H, complex CHCONH and C$_6$-proton), 6.7–7.8 (4H, complex, thienyl, and —NH— protons).

The disodium salt was precipitated from acetone with 2 N ethyl hexoate in methyl isobutyl ketone (0.34 ml.).

What we claim is:

1. The process which comprises reacting a 7-acylaminocephalosporin of the formula:

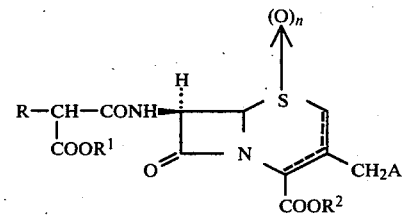

wherein
R is furyl, thienyl, cycloalkyl of 3 to 7 carbon atoms cycloalkenyl of 3 to 7 carbon atoms, phenyl or phenyl substituted with from 1 to 3 members selected from the group consisting of hydroxy, halo, nitro, alkyl of 1 to 6 carbon atoms, amino and carboxy;
R$^1$ is alkyl of 1 to 6 carbon atoms, benzyl, phthalidyl, indanyl, phenyl, or phenyl substituted with from 1 to 3 alkyl groups of 1 to 6 carbon atoms;
R$^2$ is hydrogen an in vivo hydrolysable ester group selected from the group consisting of acyloxyalkyl, alkoxycarbonloxyalkyl, lactone, thiolactone and dithiolactone or a chemically hydrolysable carboxy blocking group;
A is hydrogen, pyridyl, acetoxy, carbamoyloxy, or S-Het wherein Het is diazolyl, triazolyl, tetrazolyl, thiazolyl, thiadiazolyl, thiatriazolyl, oxazolyl or oxadiazolyl, unsubstituted or substituted with one or two members selected from the group consisting of alkyl of 1 to 6 carbon atoms, alkenyl of 1 to 6 carbon atoms, alkoxy of 1 to 6 carbon atoms, alkoxyalkyl, carboxyalkyl, carbamoyl, carbamoylmethyl, trifluoromethyl, hydroxy and halo;
n is zero or 1; and
the dotted line represents a double bond at either the 2- or 3- position,
with an acid halide, thereby forming a ketenimine of the formula:

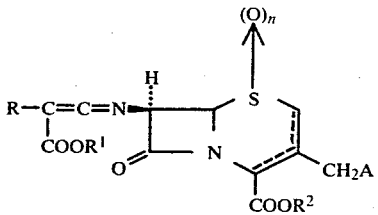

wherein R, $R^1$, $R^2$, A and n and the dotted line are as herein defined.

2. The process which comprises treating a ketenimine of the formula

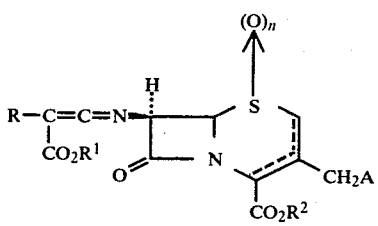

wherein

R is furyl, thienyl, cycloalkyl of 3 to 7 carbon atoms cycloalkenyl of 3 to 7 carbon atoms phenyl or phenyl substituted with from 1 to 3 members selected from the group consisting of hydroxy, halogen, nitro, alkyl of 1 to 6 carbon atoms, amino and carboxy;

$R^1$ is alkyl of 1 to 6 carbon atoms, benzyl, phthalidyl, indanyl, phenyl, or phenyl substituted with from 1 to 3 alkyl groups of 1 to 6 carbon atoms;

$R^2$ is hydrogen an in vivo hydrolysable ester group selected from the group consisting of acyloxyalkyl, alkoxycarbonloxyalkyl, lactone, thiolactone and dithiolactone or a chemically hydrolysable carboxy blocking group;

A is hydrogen, pyridyl, acetoxy, carbamoyloxy, or S-Het wherein Het is diazolyl, triazolyl, tetrazolyl, thiazolyl, thiadiazolyl, thiatriazolyl, oxazolyl or oxadiazolyl, unsubstituted or substituted with one or two members selected from the group consisting of alkyl of 1 to 6 carbon atoms, alkenyl of 1 to 6 carbon atoms, alkoxy of 1 to 6 carbon atoms, alkoxyalkyl, carboxyalkyl, carbamoyl, carbamoylmethyl, trifluoromethyl, hydroxy and halo;

n is zero or 1; and the dotted line represents a double bond at either the 2- or 3- position, with a double bond addition agent and treating the resultant adduct with a methoxide of the formula $CH_3OM$ where M is an alkali metal or thallium.

3. The process which comprises treating a compound of the formula

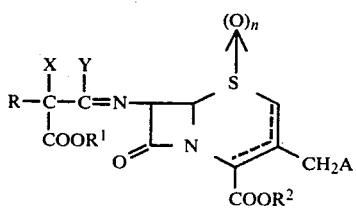

wherein

R is furyl, thienyl, cycloalkyl of 3 to 7 carbon atoms cycloalkenyl of 3 to 7 carbon atoms phenyl or phenyl substituted with from 1 to 3 members selected from the group consisting of hydroxy, halogen, nitro, alkyl of 1 to 6 carbon atoms, amino and carboxy;

$R^1$ is alkyl of 1 to 6 carbon atoms, benzyl, phthalidyl, indanyl, phenyl, or phenyl substituted with from 1 to 3 alkyl groups of 1 to 6 carbon atoms;

$R^2$ is hydrogen an in vivo hydrolysable ester group selected from the group consisting of acyloxyalkyl, alkoxycarbonloxyalkyl, lactone, thiolactone and dithiolactone or a chemically hydrolysable carboxy blocking group;

A is hydrogen, pyridyl, acetoxy, carbamoyloxy, or S-Het wherein Het is diazolyl, triazolyl, tetrazolyl, thiazolyl, thiadiazolyl, thiatriazolyl, oxazolyl or oxadiazolyl, unsubstituted or substituted with one or two members selected from the group consisting of alkyl of 1 to 6 carbon atoms, alkenyl of 1 to 6 carbon atoms, alkoxy of 1 to 6 carbon atoms, alkoxyalkyl, carboxyalkyl, carbamoyl, carbamoylmethyl, trifluoromethyl, hydroxy and halo;

n is zero or 1; and the dotted line represents a double bond at either the 2- or 3- position, and X and Y are the radicals of a double bond addition reagent, with a methoxide of the formula $CH_3OHM$ where M is an alkali metal or thallium, thereby forming a 7-methoxyketenimine of the formula:

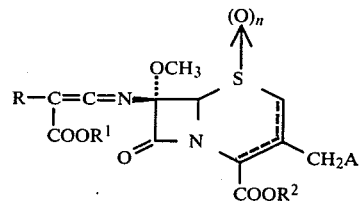

wherein R, $R^1$, $R^2$, A, n and the dotted line are as herein defined.

4. The process which comprises hydrolysing a 7-methoxyketenimine of the formula:

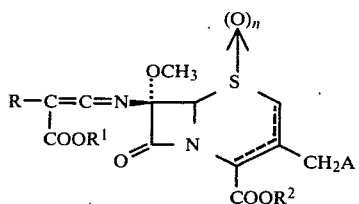

wherein

R is furyl, thienyl, cycloalkyl of 3 to 7 carbon atoms cycloalkenyl of 3 to 7 carbon atoms phenyl or phenyl substituted with from 1 to 3 members selected from the group consisting of hydroxy, halogen, nitro, alkyl of 1 to 6 carbon atoms, amino and carboxy;

$R^1$ is alkyl of 1 to 6 carbon atoms, benzyl, phthalidyl, indanyl, phenyl, or phenyl substituted with from 1 to 3 alkyl groups of 1 to 6 carbon atoms;

$R^2$ is hydrogen, an in vivo hydrolysable ester group selected from the group consisting of acyloxyalkyl, alkoxycarbonloxyalkyl, lactone, thiolactone and dithiolactone or a chemically hydrolysable carboxy blocking group;

A is hydrogen, pyridyl, acetoxy, carbamoyloxy, or S-Het wherein Het is diazolyl, triazolyl, tetrazolyl, thiazolyl, thiadiazolyl, thiatriazolyl, oxazolyl or oxadiazolyl, unsubstituted or substituted with one or two members selected from the group consisting of alkyl of 1 to 6 carbon atoms, alkenyl of 1 to 6 carbon atoms, alkoxy of 1 to 6 carbon atoms, alkoxyalkyl, carboxyalkyl, carbamoyl, carbamoylmethyl, trifluoromethyl, hydroxy and halo;

n is zero or 1; and the dotted line represents a double bond at either the 2- or 3-position, thereby forming a compound of the formula:

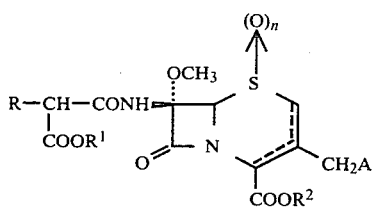

wherein R, $R^1$, $R^2$, A, n and the dotted line are as herein defined.

5. In the process for the preparation of a compound of the formula:

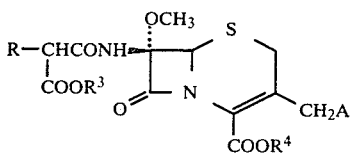

wherein

R is furyl, thienyl, cycloalkyl of 3 to 7 carbon atoms cycloalkenyl of 3 to 7 carbon atoms phenyl or phenyl substituted with from 1 to 3 members selected from the group consisting of hydroxy, halogen, nitro, alkyl of 1 to 6 carbon atoms, amino and carboxy;

$R^3$ is hydrogen, a pharmaceutically acceptable salt-forming ion, benzyl, phthalidyl, indanyl, phenyl, or phenyl substituted with from 1 to 3 alkyl groups of 1 to 6 carbon atoms;

$R^4$ is hydrogen, a pharmaceutically acceptable salt-forming ion or an in vivo hydrolysable ester-forming radical; and A is hydrogen, pyridyl, acetoxy, carbamoyloxy, or S-Het wherein Het is diazolyl, triazolyl, tetrazolyl, thiazolyl, thiadiazolyl, thiatriazolyl, oxazolyl or oxadiazolyl, unsubstituted or substituted with one or two members selected from the group consisting of alkyl of 1 to 6 carbon atoms, alkenyl of 2 to 6 carbon atoms, alkoxy of 1 to 6 carbon atoms, alkoxyalkyl, carboxyalkyl, carbamoyl, carbamoylmethyl, trifluoromethyl, hydroxy and halo;

the step which comprises hydrolysing a 7α-methoxy ketenimine of the formula

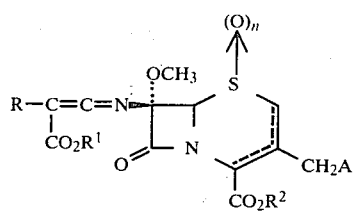

wherein A and R are as herein defined, $R^1$ is benzyl, phthalyl, indanyl, phenyl or phenyl substituted with from 1 to 3 alkyl groups of 1 to 6 carbon atoms;

$R^2$ is hydrogen an in vivo hydrolysable ester group selected from the group consisting of acyloxyalkyl, alkoxycarbonloxyalkyl, lactone, thiolactone and dithiolactone or a chemically hydrolysable carboxy blocking group;

n is zero or 1; and the dotted line represents a double bond at either the 2- or 3-position to form the corresponding 7-acylaminocephalosporin and thereafter removing any carboxyl-blocking groups, converting any $\Delta^2$ isomer present to the $\Delta^3$ isomer and reducing any sulphoxide compound where n=1 to the corresponding sulphide where n=0.

6. In the process for the preparation of a compound of the formula:

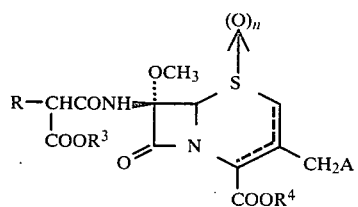

in which

R is 2-thienyl, 3-thienyl, phenyl or hydroxyphenyl;

$R_3$ is hydrogen or a pharmaceutically acceptable cation;

$R^4$ is hydrogen, a pharmaceutically acceptable cation or an in vivo hydrolysable ester forming group; and A is acetoxy or 1-methyl-(1H)-tetrazol-5-ylthio, the steps which comprise reacting a 7-acylaminocephalosporin of the formula:

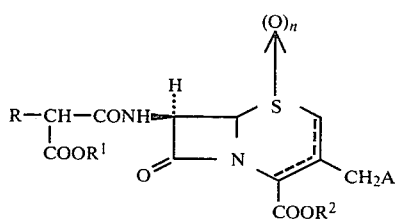

wherein

R and A are as defined above;

$R^1$ is alkyl of 1 to 6 carbon atoms, benzyl, phthalidyl, indanyl, phenyl or phenyl substituted with from 1 to 3 alkyl groups of 1 to 6 carbon atoms;

$R^2$ is an in vivo hydrolysable ester forming radical or a carboxy-blocking group;

n is zero or 1; and the dotted line represents a double bond at either the 2- or the 3-position, with an acid halide selected from the group consisting of phosphorus pentachloride, phosgene, phosphorus pentabromide, phosphorus oxychloride, oxalyl chloride or p-toluenesulphonic acid chloride to form the corresponding ketenimine, treating said ketenimine with a halogen to form a dihalo adduct, treating said adduct in situ with an alkali metal methoxide to form a 7-methoxyketenimine, hydrolyzing said 7-methoxyketenimine to yield a compound of the formula:

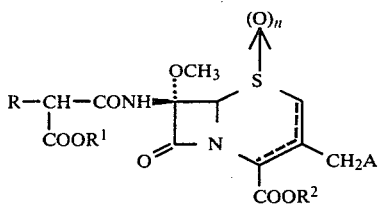

wherein R, $R^1$, $R^2$, A, n and the dotted line are as herein defined.

7. A process according to claim 1 wherein the acid halide is phosphorus pentachloride, phosgene, phosphorus pentabromide, phosphorus oxychloride, oxalyl chloride or p-toluenesulphonic acid chloride.

8. A process according to claim 1 in which said reaction is carried out in the presence of a tertiary amine.

9. A process according to claim 5 wherein the hydrolysis is carried out at a pH of from 2 to 4.

10. A process according to claim 3 wherein each of X and Y is halogen.

11. A process according to claim 2 wherein the double bond addition reagent is a halogen.

12. The process according to claim 1 including the step of treating said ketenimine with a double bond addition reagent of the formulas X-Y to form an adduct product of the formula:

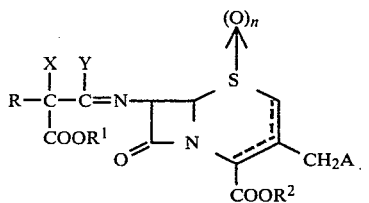

wherein
R, $R^1$, $R^2$, A, n and the dotted line are as herein defined; and

X and Y are the radicals of the double bond addition reagent, and treating said addition product with a compound of the formula $CH_3OM$ where M is an alkali metal or thallium, thereby forming a 7-methoxyketenimine of the formula:

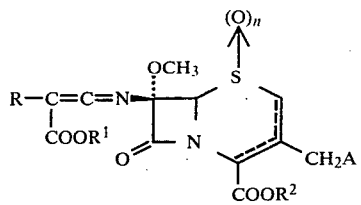

wherein R, $R^1$, $R^2$, A, n and the dotted line are as therein defined.

13. The process according to claim 1 including the step of hydrolyzing said 7-methoxyketenimine, thereby forming a 7α-methoxy-7β-acylamino compound of the formula:

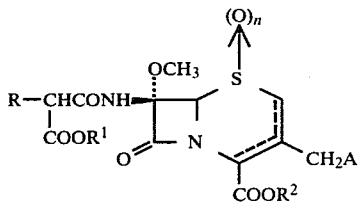

wherein R, $R^1$, $R^2$, A, n and the dotted line are as therein defined.

14. The process according to claim 2 wherein said adduct is treated with said methoxide without isolation of said adduct.

15. The process according to claim 3 including the step of hydrolyzing said 7-methoxyketenimine, thereby forming a 7α-methoxy-7β-acylamino compound of the formula:

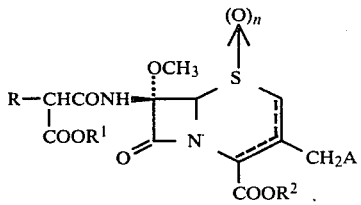

wherein R, $R^1$, $R^2$, A, n and the dotted line are as therein defined.

* * * * *